(12) United States Patent
Hsu et al.

(10) Patent No.: US 6,455,249 B1
(45) Date of Patent: Sep. 24, 2002

(54) METHOD OF AMPLIFYING DNA AND RNA MISMATCH CLEAVAGE PRODUCTS

(75) Inventors: Ih-Chang Hsu, Ellicott City, MD (US); William E. Highsmith, Jr., Baltimore, MD (US); James Shih, Potomac, MD (US)

(73) Assignees: National Institutes of Health, Bethesda, MD (US); University of Maryland Baltimore, Baltimore, MD (US)

( * ) Notice: Subject to any disclaimer, the term of this patent is extended or adjusted under 35 U.S.C. 154(b) by 0 days.

(21) Appl. No.: 09/150,661

(22) Filed: Sep. 10, 1998

Related U.S. Application Data

(60) Provisional application No. 60/058,419, filed on Sep. 10, 1997.

(51) Int. Cl.[7] .................................................. C12Q 1/68
(52) U.S. Cl. .......................................... 435/6; 536/23.1
(58) Field of Search ............................... 435/6; 536/23.1

(56) References Cited

U.S. PATENT DOCUMENTS

| | | | |
|---|---|---|---|
| 5,556,750 A | | 9/1996 | Modrich et al. ................ 435/6 |
| 5,656,430 A | * | 8/1997 | Chirikjian et al. ............. 435/6 |
| 5,683,877 A | | 11/1997 | Hsu ................................. 435/6 |
| 5,763,178 A | | 6/1998 | Chirikjian et al. ............. 435/6 |
| 5,858,665 A | | 1/1999 | Hepp et al. ..................... 435/6 |

FOREIGN PATENT DOCUMENTS

WO     WO 93/20233     10/1993

OTHER PUBLICATIONS

"Use of MutY and thymine glycosylase to detect point mutations" in: Taylor, G.R. (Ed.), The Detection of DNA Sequence Polymorphisms and Mutations: Methods and Application, CRC Press, Inc. pp. 195–206.
14 *Genomics* 249 1992 Lu, Hsu.
15 *Carcinogenesis* 8:1657 1994 Hsu et al.
17 *Carcinogenesis* 2:321 1996 Xu et al.
25 *BioTechniques* 4:692 1998 Hsu et al.
261 *Analytical Biochemistry* 219 1998 Hsu et al.

\* cited by examiner

*Primary Examiner*—Eggerton A. Campbell
(74) *Attorney, Agent, or Firm*—Max Stul Oppenheimer

(57) ABSTRACT

Detection of probe fragment products of basepair mismatch cleavage indicate the presence and sequence of target DNA. Detection of the target is enhanced by amplification through recycling targets by maintaining an assay temperature between the melting point of the target/probe DNA duplex and that of the target/product complex, in the presence of an amplifier comprising ammonium acetate or an amine derivative (for example, diethylamine, piperidine or ammonium carbonate). Cleavage reduces the size of the duplex, and thus lowering its melting point. The amplifier releases the target from the complex, thereby permitting further catalysis of cleavage and effectively amplifying the signal to be detected.

25 Claims, 11 Drawing Sheets

SEQUENCE LISTING

```
<160> NUMBER OF SEQ ID NOS: 8

<210> SEQ ID NO 1
<211> LENGTH: 24
<212> TYPE: DNA
<213> ORGANISM: Human breast tumor cell line

<400> SEQUENCE: 1
ctgccctcaa caagatgttt tgcc                                            24

<210> SEQ ID NO 2
<211> LENGTH: 21
<212> TYPE: DNA
<213> ORGANISM: Human cystic fibrosis

<400> SEQUENCE: 2
ataggaaaca acaatgatat t                                               21
```

-continued

```
<210> SEQ ID NO 3
<211> LENGTH: 21
<212> TYPE: DNA
<213> ORGANISM: Human immunodeficiency virus

<400> SEQUENCE: 3
ccatagtgct tactgctgct c                                         21

<210> SEQ ID NO 4
<211> LENGTH: 19
<212> TYPE: DNA
<213> ORGANISM: Human cytomegalovirus

<400> SEQUENCE: 4
gcgtgaagaa agtgattcc                                            19

<210> SEQ ID NO 5
<211> LENGTH: 20
<212> TYPE: DNA
<213> ORGANISM: Human breast tumor cell line

<400> SEQUENCE: 5
ttcaactctg tctccttcct                                           20

<210> SEQ ID NO 6
<211> LENGTH: 20
<212> TYPE: DNA
<213> ORGANISM: Human breast tumor cell line

<400> SEQUENCE: 6
tgtgcagggt ggcaagtggc                                           20

<210> SEQ ID NO 7
<211> LENGTH: 22
<212> TYPE: DNA
<213> ORGANISM: Human cystic fibrosis

<400> SEQUENCE: 7
gcaccattaa agaaaatatg at                                        22

<210> SEQ ID NO 8
<211> LENGTH: 20
<212> TYPE: DNA
<213> ORGANISM: Human cystic fibrosis

<400> SEQUENCE: 8
cattcacagt agcttaccca                                           20
```

METHOD OF AMPLIFYING DNA AND RNA MISMATCH CLEAVAGE PRODUCTS

CROSS REFERENCE TO RELATED APPLICATIONS

This application claims priority to U.S. Provisional Patent Application Ser. No. 60/058,419, filed Sep. 10, 1997.

The development of the present invention was supported by the University of Maryland, Baltimore and the Public Health Service. Certain studies described herein were supported by a grant from the Environmental Protection Agency, EPA Grant No. R-818 104-01. The Government may have certain rights.

FIELD OF THE INVENTION

The present invention generally relates to detection of nucleic acid sequence mutations. The present invention more specifically relates to a new and useful method for signal amplification of mismatch cleavage.

BACKGROUND OF THE INVENTION

The ability to detect alterations in nucleic acid sequences (for example, mutations and polymorphisms) is central to the diagnosis of genetic diseases and to the identification of clinically significant variants of disease-causing microorganisms. Similarly, identification and measurement of RNA is necessary for determining control of gene transcription.

One method for the molecular analysis of genetic variation involves the detection of restriction fragment length polymorphisms (RFLPs) using the Southern blotting technique (Southern, E. M., *J. Mol. Biol.*, 98 503–517, 1975). Since this approach is relatively cumbersome, new methods have been developed, some of which are based on the polymerase chain reaction (PCR).

These include: RFLP analysis using PCR (Chehab et al., *Nature*, 329, 293–294, 1987; Rommens et al., *Am. J. Hum. Genet.*, 46, 395–396, 1990), allele-specific amplification (ASA) (Newton C R et al., *Nuc. Acids Res.*, 17, 2503–2516, 1989), oligonucleotide ligation assay (OLA) (Landergren U et al., *Science* 241, 1077–1080, 1988), primer extension (Sokolov B P, *Nucl. Acids Res.*, 18, 3671, 1989), artificial introduction of restriction sites (AIRS) (Cohen L B et al., *Nature* 334, 119–121, 1988), allele-specific oligonucleotide hybridization (ASO) (Wallace R B et al., *Nucl. Acids Res.*, 9, 879–895, 1981) and their variants.

The following are further examples of art discussing mismatch repair enzymes and systems utilizing such enzymes in addition to other related subject matter:

Lu et al., 80 *Proc. Natl. Acad. Sci. USA* 4639, 1983 disclose the use of a soluble *E. coli* system to support mismatch correction in vitro.

Pans et al., 163 *J. Bact.* 1007, 1985 disclose cloning of the mutS and mutL genes of *Salmonella typhimurium*.

The specific components of the *E. coli* mispair correction system have been isolated and the biochemical functions determined. Preparation of MutS protein substantially free of other proteins has been reported (Su and Modrich, 1986, *Proc. Nat. Acad. Sci. U.S.A.*, 84, 5057–5061. The isolated MutS protein was shown to recognize four of the eight possible mismatched base pairs (specifically, G-T, A-C, A-G and C-T mispairs).

U.S. Pat. No. 5,556,750 ("Methods and kits for fractionating a population of DNA molecules based on the presence or absence of a base-pair mismatch utilizing mismatch repair systems, issued Sep. 17, 1996 to Duke University) describes methods of fractionating DNA molecules based on base-pair mismatch utilizing mismatch repair systems.

Su et al., 263 *J. Biol. Chem.* 6829, 1988 disclose that the mutS gene product binds to each of the eight base pair mismatches and does so with differential efficiency.

Jiricny et al., 16 *Nucleic Acids Research* 7843, 1988 disclose binding of the mutS gene product of *E. coli* to synthetic DNA duplexes containing mismatches to correlate recognition of mispairs and efficiency of correction in vivo. Nitrocellulose filter binding assays and band-shift assays were utilized.

Welsh et al., 262 *J. Biol. Chem.* 15624, 1987 purified the product of the MutH gene to near homogeneity and demonstrated the MutH gene product to be responsible for d(GATC) site recognition and to possess a latent endonuclease that incises the unmethylated strand of hemimethylated DNA 5' to the G of d(GATC) sequences.

Au et al., 267 *J. Biol. Chem.* 12142, 1992 indicate that activation of the MutH endonuclease requires MutS, MutL and ATP.

Grilley et al. 264 *J. Biol. Chem.* 1000, 1989 purified the *E. coli* mutL gene product to near homogeneity and indicate that the mutL gene product interacts with MutS heteroduplex DNA complex.

Lahue et al., 245 *Science* 160, 1989 delineate the components of the *E. coli* methyl-directed mismatch repair system that function in vitro to correct seven of the eight possible base pair mismatches. Such a reconstituted system consists of MutH, MutL, and MutS proteins, DNA helicase II, single-strand DNA binding protein, DNA polymerase III holoenzyme, exonuclease I, DNA ligase, ATP, and the four deoxyribonucleoside triphosphates.

Su et al., 31 *Genome* 104, 1989 indicate that under conditions of restricted DNA synthesis, or limiting concentration of dNTPs, or by supplementing a reaction with a ddNTP, there is the formation of excision tracts consisting of single-stranded gaps in the region of the molecule containing a mismatch and a d(GATC) site.

Grilley et al. 268 *J. Biol. Chem.* 11830, 1993, indicate that excision tracts span the shorter distance between a mismatch and the d(GATC) site, indicating a bidirectional capacity of the methyl-directed system.

Holmes et al., 87 *Proc. Natl. Acad. Sci. USA*, 5837, 1990, disclose nuclear extracts derived from HeLa and Drosophila melanogaster K[c] cell lines to support strand mismatch correction in vitro.

Cooper et al., 268 *J. Biol. Chem.*, 11823, 1993, describe a role for RecJ and Exonuclease VII as a 5' to 3' exonuclease in a mismatch repair reaction. In reconstituted systems such a 5' to 3' exonuclease function had been provided by certain preparations of DNA polymerase III holoenzyme.

Au et al., 86 *Proc. Natl. Acad. Sci. USA* 8877, 1989 describe purification of the mutY gene product of *E. coli* to near homogeneity, and state that the MutY protein is a DNA glycosylase that hydrolyzes the glycosyl bond linking a mispaired adenine (G-A) to deoxyribose. However, their enzyme did not cleave the A strand at "A" in a circular closed heteroduplex DNA with G/A mismatch as a substrate. The MutY protein, DNA polymerase I, and DNA ligase were shown to reconstitute G-A to G-C mismatch correction in vitro in the presence of an apurinic endonuclease.

Tsai-Wu et al., 89 *Biochemistry* 8779, 1992, cloned mutY gene, overexpress and purified the MutY enzyme to homogeneity for examining enzyme specificity. In addition to glycosylase activity, this MutY enzyme can cleave the "A" of G/A mismatch on the A strand.

Wiebauer and Jiricny, 339 *Nature* 234, 1989, discovered the correction of G/T mispairs to G/C pairs by thymine DNA glycosylase in human cells.

Nedderman and Jiricny, 268 *J. Biol. Chem.* 21218, 1993, purified the G/T mnispair specific thymine glycosylase from HeLa cells.

Slupsker et al., 178, *J. Bacteriol.* 3885, 1996, cloned and sequenced a human homolog (hMYH) of *E. coli* mutY gene whose function is the repair of oxidative DNA damage.

A role for the *E. coli* mismatch repair system in controlling recombination between related but non-allelic sequences has been indicated (Feinstein and Low, 113 *Genetics*, 13, 1986; Rayssiguier, 342 *Nature* 396, 1989; Shen, 218 *Mol. Gen. Genetics* 358, 1989; Petit, 129 *Genetics* 327, 1991). The frequency of crossovers between sequences which differ by a few percent or more at the base pair level are rare. In bacterial mutants deficient in methyl-directed mismatch repair, the frequency of such events increases dramatically. The largest increases are observed in MutS and MutL deficient strains. (Rayssiguier, supra; and Petit, supra.)

Nelson et al., 4 *Nature Genetics* 11, 1993, disclose a genomic mismatch (GMS) method for genetic linkage analysis. The method allows DNA fragments from regions of identity-by-descent between two relatives to be isolated based on their ability to form mismatch-free hybrid molecules.

During the last few years, a group of bacteria repair enzymes, e.g., endo VIII (Melamede, et al., *Biochemistry*, 33, 1255–1264, 1994), endo III (Dizdaroglu et al., *Biochemistry*, 32, 12105–12111, 1993), formamidopyrimidine-DNA glycosylase (Chetsanga et al., *Biochemistry*, 20, 5201–5207, 1981), T4 endonuclease V (Nakabeppu et al., *J. Biol. Chem.*, 257, 2556–2562, 1982; McCullough et al., *J. Biol. Chem.*, 272, 27210–27217, 1997), etc., have been isolated and characterized to repair the damaged and modified nucleic acid base. Like MutY and thymine glycosylase, these enzymes have a common repair mechanism of DNA N-glycosylase/AP lyases activity. The present invention is not limited to a specific repair enzyme. The use of these and other repair enzymes is contemplated by the invention and is consistent with the description below.

SUMMARY OF THE INVENTION

The present invention encompasses methods of amplification useful in the detection of specific genes, RNA transcripts and other DNA or RNA fragments. Specifically, the method of the invention is useful with detection methods which utilize labeled probes which bind with specificity to target molecules and which are complementary to the target with the exception of a mismatch site (e.g., the G/A or G/T basepairs) and which utilize a mismatch repair (MR) enzyme, which cleave only against the mismatch site of the double stranded complex.

For biological samples, the method of detection of the targets in genetic diseases or infectious microorganism needs a sensitivity of a million or less target DNA molecules in order to be practically useful.

In accordance with the invention, this high sensitivity is achieved by amplification of the products of the labeled probes cleaved from complementary DNA or RNA targets by mismatch repair (MR) enzymes, by recycling the target molecule. The assay temperature is set between the melting point (Tm) of the hybridized target/probe DNA duplex and that of the target/product complex. Upon cleavage of the probe by the MR enzyme, the invention utilizes amplifiers such as ammonium acetate (AA) or amiine derivatives (examples of which include, but are not limited to, diethylamine, piperidine and ammonium carbonate) to release the target DNA from the MR enzyme-target/product complex so that the target can again hybridize with intact probe molecules to form a target/probe duplex which is then also cleaved by MR enzyme and released from the MR enzyme. By the method of the invention, amplification of deoxyoligomer probe cleavage products results in greatly enhanced sensitivity.

The method of the invention, works similarly with RNA targets. Deoxyoligomer probes hybridize to target RNA to form a deoxyoligomer/RNA heterocomplex with a G/A mismatch site. The deoxyoligomer probe is cleaved at the "A" base of the mismatch site by the MR enzyme. The target RNA is freed from MR enzyme as described above for DNA targets and is so similarly able to again participate in target/probe hybridization. Amplification of the RNA signal by this method facilitates G/A basepair analysis of RNA transcripts in Northern analysis or retro viruses.

The various features of novelty which characterize the invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

DETAILED DESCRIPTION OF THE INVENTION

Figure 1:
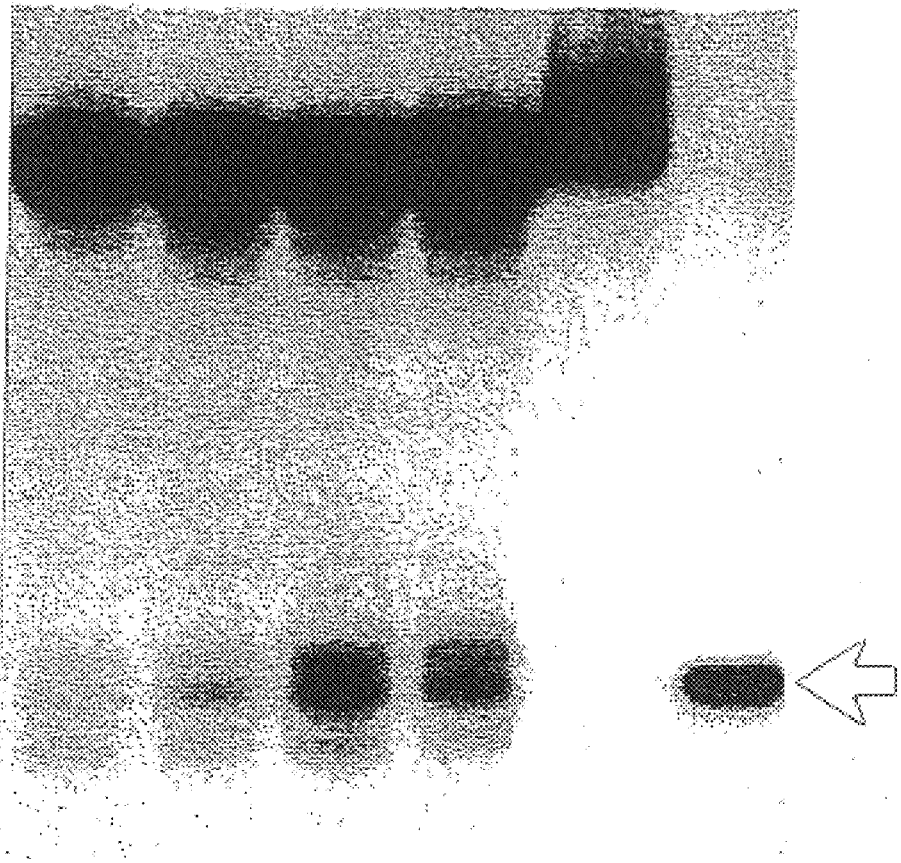
FIG. 1 is a gel showing the effects of biot 333 DNA and AA on MutY enzyme mismatch cleavage.

In mismatch repair detection systems, synthetic deoxyoligomer probes are typically used that hybridize complementary DNA targets and generate mismatches for mismatch repair (MR) enzyme cleavage. The specific MR cleavage and the size of the cleaved probe identify the site and nature of a mutation or a specific DNA sequence (for example, a genetic mutation or an infectious microorganism).

For biological samples, the detection of the targets in genetic diseases or infectious agents by mismatch cleavage needs to be sensitive enough to detect a million or fewer target DNA molecules. In the prior art, the target DNA fragments are amplified by polymerase chain reaction (PCR).

The present invention recycles the targets to dramatically increase the sensitivity of any mismatch repair assay. This is accomplished by setting the assay temperature between the Tm of target/probe DNA duplex and that of target/product complex. The cleavage of the probe reduces its size, thereby lowering the Tm and thus releasing the target. However, the enzyme binds to the target-product complex and does not separate the target from the complex even after the cleavage of the probe.

In accordance with the present invention, ammonium acetate or one of its amine derivatives is provided, thereby releasing the target from the MR enzyme so that it can reengage hybridized probe/target complexes and catalyze the cleavage again, thus effectively amplifying the number of target signals for detection.

Experiments have shown the recycling of the target DNA by demonstrating that the use of an amplifier produces much more cleaved DNA probe than the target DNA at the end of the assay. As a result, a 100–1000 fold increase of sensitivity is obtained at 37° C. The amplifier does not activate the enzyme to increase sensitivity. When a probe is large and the Tm of DNA duplex for target/probe or the target/cleaved probe is more than 37° C., the amplifier indeed reduces some enzyme activity. The amplification of mismatch cleavage of the probe improves the detection of a human immunodeficiency virus (HIV) target and mutated human DNA sequences such as the most frequently occurring three base deletion at codon 508 of the human Cystic fibrosis gene (ΔF508 mutant). Additionally, the amplification is observed in the cleavage of the deoxyoligomer probe at the mismatch of a DNA/RNA heteroduplex i.e., the probe and the RNA transcript of Hepatitis C virus (HCV) target. At 37° C. with amplification, approximately a million mutated CF DNA molecules can be detected. The assay, when used at higher temperatures with a thermally stable MR enzyme, can further increase the sensitivity.

The following examples of experiments will further illustrate the invention.

EXAMPLES

Enzymes, Chemicals, and Reagents

MutY mismatch repair (MR) enzyme was overproduced in *E. coli* HMS 174 host that harbored a mutY enzyme overexpression vector. The procedures of preparation, isolation, and purification of MutY protein are described in Xu, J. F. et al., *Carcinogenesis*, 1996, 17, 321–326).

Quick spin columns (0.6×3 cm containing sephadex G 25 gel), Tris, EDTA, SDS and T4-polynucleotide kinase (PNK) were purchased from Boehringer Mannheim (Indianapolis, Ind.). [r-$^{32}$P]ATP (3000 Ci/mmole) and acrylamide were obtained from Amersham (Arlington Heights, Ill.) and Bio-Rad (Hercules, Calif.), respectively.

Probes and Targets

The target DNA fragments were prepared by PCR amplification of genomic DNAs from BT20 cells (Bartek, J., et al., *Oncogene*, 5, 893–899, 1988) and from a mutant ΔF508 human sample (Zielenski, J., et al., *Genomics*, 10, 214–228, 1991). BT20 is a human breast tumor cell line with a A:T to C:G p53 mutation at codon 132 position 1. The ΔF508 mutant DNA has a homozygous 3 base deletion at codon 508 that occurs most frequently in CF patients. The HIV 1 subtype B target was obtained from qb, Inc. (Gaithersburg, Md.). It is approximately 7,300 bp containing the gene of HIV 1 subtype B GP160 envelope cloned in JM109 plasmid (Gao, F., et al., *J. Virol.*, 70, 1651–1657, 1996).

The primers for PCR preparations of the 1112 bp BT20 target and the 219 bp CF target are listed in Table 1B below. The four oligomer probes were prepared by oligonucleotide synthesizer by Cruachem Inc. (Dallas, Va.); their sequences are listed in Table 1A below. The deoxyoligomer probe is complementary to the target DNA sequence except the "A" in bold type with underline. The probe hybridizes the target DNA and generates a G/A mismatch. The "A" for cleavage is typically located near the center of the probe. The melting temperatures (Tm) for the hybridized probes and the products are also listed in Table 1A. The DNA probes that contained the "A" for cleavage were $^{32}$P-labeled at the 5' end by a T4 polynucleotide kinase reaction. For the reaction, approximately 2–3 pmole of [r-$^{32}$P]ATP and 5–10 pmole of synthesized deoxyoligomer were incubated at 37° C. for 1 hr with 20 units of PNK in 20 ul of Tris-buffer (pH 7.8) provided by the manufacturer (Boehringer Mannheim, St. Louis, Mo.; cat. No. 838923).

TABLE 1A

Names and DNA information for the probes

| Name of probe | DNA Sequence | Tm (° C.) of probe[1] | Tm (°C.) of cleaved probes[2] |
|---|---|---|---|
| BT-20 | 5'-CTG CCC TCA ACA AGA TGT TTT GCC-3' (SEQ ID NO: 1) | 68 | 36, 34 |
| ΔF508 | 5'-ATA GGA AAC AAC AAT GAT ATT-3' (SEQ ID NO: 2) | 47 | 24, 26 |
| HIV-1b | 5'-CCA TAG TGC TTA CTG CTG CTC-3' (SEQ ID NO: 3) | 56 | 30, 32 |
| HCV | 5'-GCG TGA AGA AAG TGA TTC C-3' (SEQ ID NO: 4) | 44[4] | 28, 26 |

[1]Tm (° C.) for the probe/target DNA duplex with one miscmatch was obtained Oligo from data base (NBI, Plymouth, MN).
[2]Tm (° C.) was calculated by 2 (A + T) + 4(G + C) method for DNA duplex.
[3]A is the site of the mismatch and the base to be removed.
[4]The Tm (° C.) for RNA/DNA hybrid is higher than that for DNA/DNA duplex of the same sequence.

TABLE 1B

Names and DNA information for the targets

| Name of target | Method and PCR primes for preparing target DNA | Size of target |
| --- | --- | --- |
| BT-20 | left: 5'-TTC AAC TCT GTC TCC TTC CT-3' (SEQ ID NO: 5)<br>right: 5'-TGT GCA GGG TGG CAA GTG GC-3' (SEQ ID NO: 6) | 1113 bp |
| ΔF508 | left: 5'-GCA CCA TTA AAG AAA ATA TGA T-3' (SEQ ID NO: 7)<br>right: 5'-CAT TCA CAG TAG CTT ACC CA-3' (SEQ ID NO: 8) | 219 bp |
| HIV-1B | HIV-1b gp160 cloned in JM 109 plasmid | 7300 bp |
| HCV | RNA target by T7 RNA transcription | 1100 bp |

The labeled DNA was purified with a G-25 quick spin column (Boehringer Mannheim, St. Louis, Mo.; cat. No. 1273949)., according to the procedures of the manufacturer's as set forth in Xu, J. F., et al., *Carcinogenesis*, 17, 321–326, 1996.

Enzyme assay for detection of target DNA

The specific cleavage of G/A mismatch at "A" by MR enzyme and the expected size of the cleaved DNA identify the target DNA sequence. These mismatches are generated by annealing the 32p labeled probe and the target DNA in MutY enzyme assay buffer (Xu, J. F., et al., *Carcinogenesis*, 17, 321–326, 1996). The mixture is heated at 90° C. for 3 min. and then cooled slowly to room temperature to generate DNA duplexes with a G/A mismatch as designed for a substrate.

In the assay, approximately 10,000–20,000 dpm of the $^{32}$P labeled heteroduplex substrate was incubated overnight (approximately 15 hrs unless specified otherwise) at 37° C. with 50 ng of the MutY enzyme preparation in 20 ul of assay buffer (20 mM Tris pH 7.6, 1 mM EDTA, and 50 ug of BSA per ml). An equal volume of dye solution is added to a 3 ul aliquot of the assay mixture to stop the reaction for electrophoresis on 20% acrylamide gel.

The following examples are provided for further illustrating various aspects and embodiments of the present invention and are in no way intended to be limiting of the scope.

Example 1

Amplification for Products of BT20 Mismatch Cleavage (MC)

BT20 is a human breast tumor cell line that has an A:T to C:G p53 mutation at codon 132 position 1. The BT20 target has previously been used as a model in determining the site and nature of a mutation (Hsu, I-C., In: Taylor, G. R. (Ed.), *The Detection of DNA Sequence Polymorphisms and Mutations: Methods and Application*, CRC Press, Inc., 1997, pp. 195–206., Bartek, J., et al., *Oncogene*, 5, 893–899, 1988). Usually, a PCR amplified DNA fragment of several hundred bp has been used as a target, although a specific DNA fragment cloned into a plasmid of several thousand bp has been used successfully. In the present method, a labeled 24 bp deoxyoligomer probe will hybridize the BT20 target to create a G/A mismatch for cleavage at "A" by MutY enzyme. FIG. 1 shows the MutY cleavage of a 24 bp BT20 probe that hybridized the PCR amplified BT20 target.

Five fmole of BT20 target (1112 bp) prepared by PCR was incubated with approximately 50 fmoles of $^{32}$p labeled BT20 probe (24 bp—see Table 1B) and MutY enzyme at 37° C. as described above. The autoradiography of the gel (FIG. 1) shows the intensity of MutY cleavage for reaction mixture containing: 1) no amplifier as control (Lane 1), 2) 50 ng biot 333 DNA amplifier (Lane 2), 3) 50 ng biot 333 DNA+AA 5 mM (Lane 3), 4) AA 5 mM (Lane 4). Lane 5 is a no target control containing probe only. Lane M is the 11 bp marker. The symbol>points to the 11 bp marker and the products.

Because the enzyme does not cut a single-stranded probe (lane 5) and the sequence of the probe is complementary to the target, the cleaved probe reveals the sequence or the identity of the target. The size of the 11 bp product (lane 1–4) confirmed the cut at "A" of the mismatch that further reveals the site as well as the nature of mutation. During the assay, a small amount of .carrier DNA was included in the reaction mixture to minimize nonspecific cleavage and background. The addition of DNA occasionally improved the sensitivity (lane 2). However, the results were inconsistent with the added DNA samples from different sources. Examination of the possible components in the DNA samples, shows that AA and other amine derivatives enhanced the sensitivity. FIG. 1 shows that the presence of carrier biot-DNA (Lane 2), AA (lane 4) and biot-DNA plus AA (lane 3) produced more cleaved probes than those of the control (lane 1) in which only probe, target and MutY are included in the assay. The improvement in sensitivity is not induced by enzyme activation with AA. AA itself can reduce some MutY activity. This was demonstrated in the assay with probes having sizes over 100 bp so that the Tm of target/probe or target/cleaved probe DNA duplexes was higher than the assay temperature.

Figure 6:
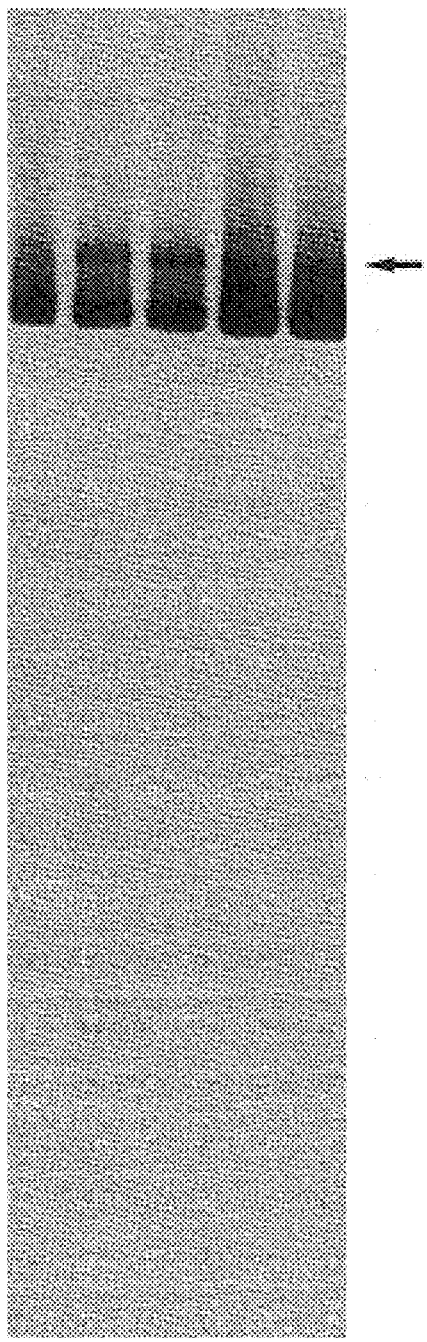
FIG. 6 is a gel showing inhibition of MutY enzyme activity by AA

The results of an experiment demonstrating the inhibition of MutY enzyme activity by AA is shown in FIG. 6. In this experiment, the target is a 201 bp DNA fragment of p53 exon 8 having a mutation at codon 287 position 2 (Kong et al., *Proc. Am. Assoc. Canc. Res.* 38, 39, 1997). It was prepared by PCR amplification of the genomic DNA sample from a paraffin-embedded human tumor sample No. 3358. The probe was prepared by the same procedure of PCR amplification above from a normal human DNA sample. The size and sequence of the probe are the same as those from the tumor 3358 sample except the site of codon 287 position 2 at which a mismatch will be generated for cleavage in the assay. The assay was carried out by the protocol described previously (Hsu, I-C., "Use of MutY and thymine glycosylase to detect point mutations." In: Taylor, G. R. (Ed.), *The*

Detection of DNA Sequence Polymorphisms and Mutations: Methods and Application, CRC Press, Inc. 1997 pp. 195–206).

FIG. 6, lane 1 is the control without enzyme in the incubation. Lanes 2 and 3 are duplicates of the assay without AA in the experiment. Lanes 4 and 5 are duplicates with 10 mM of AA in the assay mixture. Because the sizes of substrate DNA duplex and the cleaved probe are more than 80 bp, The Tms of the target and the cleaved probe are more than 50° C. and so recycling of the target is unlikely to occur at 37° C. The $^{32}$P activity in lanes 2 and 3 are stronger than that in lanes 4 and 5 for cleaved product as indicated by ">" The lower quantity of cleaved product is indicative of the inhibition of MutY activity by AA.

Many compounds have been tested for amplification of MutY sensitivity. Only AA and other amine derivatives such as diethylamine, piperidine, ammonium carbonate etc., make significant improvements of assay sensitivity, although the activities of amplification are not equal among the amine derivatives. AA and diethylamine are the best amplifiers. A possible explanation for increasing the sensitivity is that the amplifiers free the target from the enzyme complex for use again in the cleavage. The BT20 probe is 24 bp and has a Tm of 56° C. The products are 11 and 12 bp and have Tms between 34 and 35° C. (Table 1A). Therefore at 37° C. assay temperature, the Tm for target/probe DNA duplex is higher than the assay temperature whereas the Tms of the target/products are lower than the assay temperature (37° C.). Not being bound by theory, the cleaved probes, because of the lower Tm than the assay temperature, dissociates from the target. The free target hybridizes with probes again which are then themselves cleaved resulting in production of more cleaved probes. The recycling of the targets produces more cleaved probes than the targets in the assay mixture and in this manner, amplifies the sensitivity. However, without the addition of amplifier, the enzyme binds tightly to the target/probe DNA complex even after the cleavage.

Binding of MutY enzyme to the DNA heteroduplex with a G/A mismatch has been reported (Lu, A., and Chang, D., Cell, 54, 805–812, (1988), Au, K. G., et al., Proc. Nat. Acad. Sci. USA, 86, 8877–8881, (1989), Tsai-Wu, J., et al., Proc. Natl. Acad. Sci. 89, 8779–8783, (1992)). Not being bound by theory, amplifier in the assay mixture releases the target from the enzyme-target/probe complex by blocking the enzyme binding site(s) to the substrate, thereby changing the shape of enzyme-substrate complex and forcing the target out of the complex. To test the hypothesis, a smaller 21 bp probe and a 200 bp ΔF508 target was used for the assay of MutY cleavage. The hybridized probe has a Tm of 47° C., whereas the product has a Tm of 24–26° C.

Example 2

Amplification for Products of ΔF508 Mismatch Cleavage (MC)

Figure 2A:
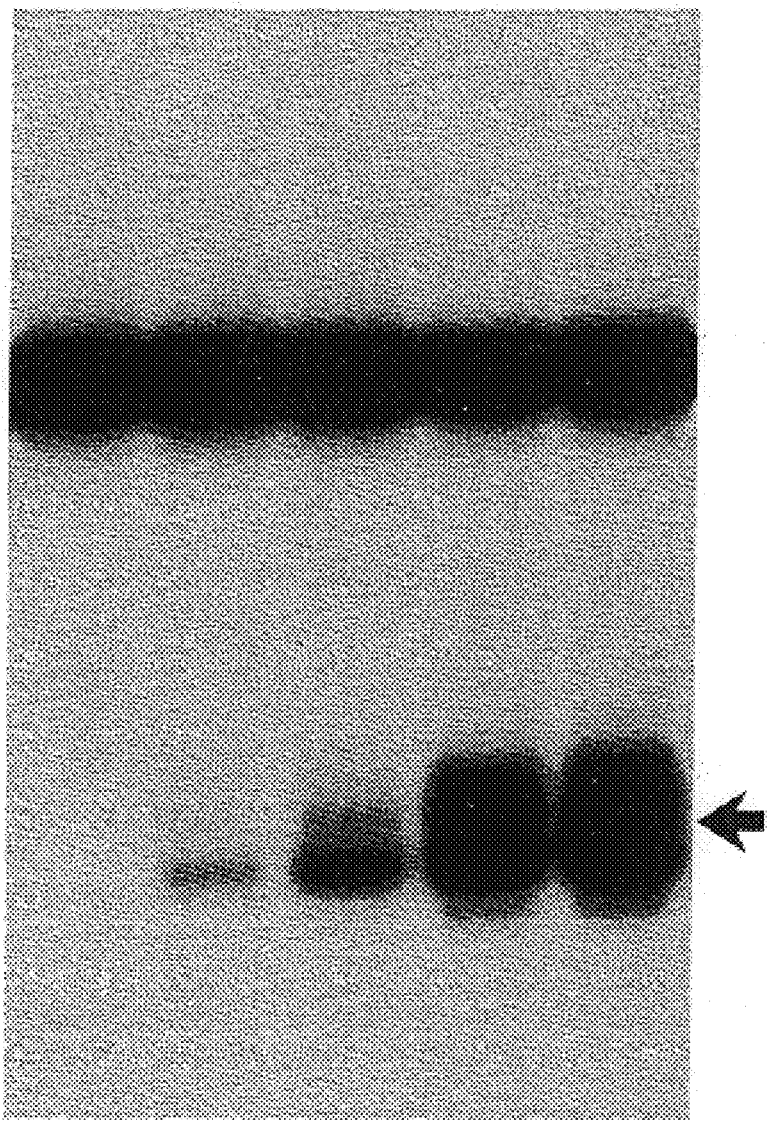
FIGS. 2A and 2B are gels showing MutY enzyme detection and amplification of ΔF508 gene, a mutant Cystic fibrosis gene.
Figure 2B:
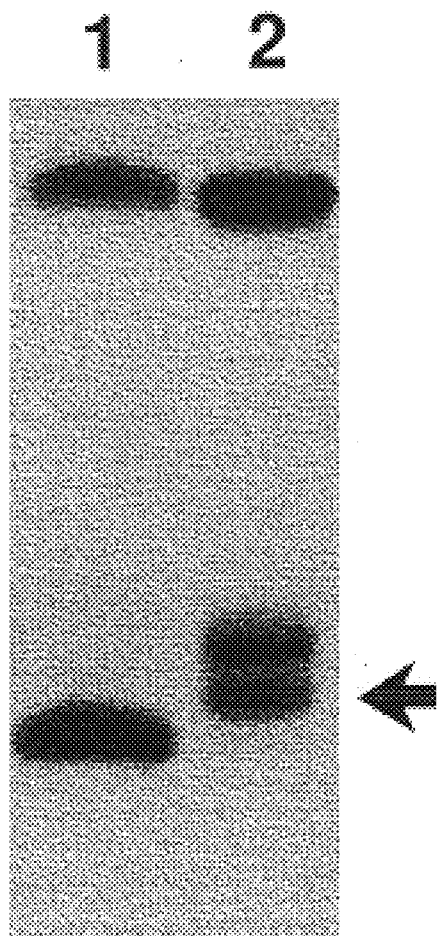

FIGS. 2A and 2B shows MutY enzyme detection and amplification of mutated CF gene, i.e., ΔF508. The mutated CF gene has a 3 base deletion at codon 508. The target is a PCR amplified 219 bp DNA fragment from the mutated CF genomic DNA (Table 1B). The 21 bp probe is complimentary to the target and will generate a G/A mismatch. The assay was carried out with 7 fmoles of target and 100 fmoles of probe as described above. FIG. 2A shows MutY cleavage at 37° C. in the reaction mixture with 0 AA (Lane 2), 7.5 mM AA (Lane 3), 75 mM AA (Lane 4) and 75 mM AA at pH 7.6 (Lane 5). Lane 1 is the control containing 75 mM AA but no target. The rest of assay mixture in lane 4 of FIG. 2A was incubated at 37° C. for another 20 hr, and divided into two portions for quantifying MutY cleavage (FIG. 2B). An equal volume of dye solution was added to the first half of reaction mixture for electrophoresis (lane 2). The other half was pretreated in 1 M piperidine at 90° C. for 30 min before adding to the dye solution for gel electrophoresis (lane 1). The cleaved probes are indicated with a > symbol.

FIG. 2A shows that MutY does not cut single-stranded DNA (lane 1). It only cuts the DNA heteroduplex at A with an A/G mismatch (lanes 2–5). The product increases with increasing concentrations of AA (lanes 2–5). Drastic increases of product were observed at 75 mM AA (lane 4) and even higher at 75 mM AA at pH 7.6 (lane 5). Thus, the results suggest that AA competes with MutY for substrate binding site and causes the release of target DNA for recycling. Once the substrate DNA binds to AA, the phosphodiester linkage can be broken at 3' or 5' end or both ends of the deoxy A (Maxam, A. M., and Gilbert, W., Methods in Enzymology, 65, 499–561, 1980). The recycling of the target is further shown in FIG. 2B in which the products are greater than the target in the reaction mixture. For the experiment, the rest of assay mixture in lane 4 of FIG. 2A was incubated at 37° C. for another 20 hrs, and divided into two portions. An equal volume of dye solution was added to the first half of assay mixture to stop the reaction for electrophoresis (lane 2). The other half was pretreated in 1 M piperidine at 90° C. for 30 min before adding an equal volume of the dye solution for gel electrophoresis (lane 1). FIG. 2B shows that the products are more than the probes left in the assay mixture. In the assay for FIG. 2, there was approximately 100 fmole of probe, but only 5–10 fmole of target. The autoradiography in FIG. 2B clearly shows that there are more cleaved DNA fragments than the probes left in the assay mixture after MutY cleavage indicating that more than 50 fmole of probe was cleaved. Since the total target in the assay was less than 10 fmole, the target must have been used again several times, i.e., recycling the target to increase the sensitivity. In addition, the products in lanes 4 and 5 are probably 20–50 fold more than those without AA in lane 2 suggesting that no release of the target occurs for recycling without AA in the reaction mixture. In contrast, the target was quickly released and recycled for amplification at 75 mM of AA (lane 4 and 5).

Example 3

Mismatch Cleavage Sensitivity for Detection of ΔF508 Target

Figure 3:
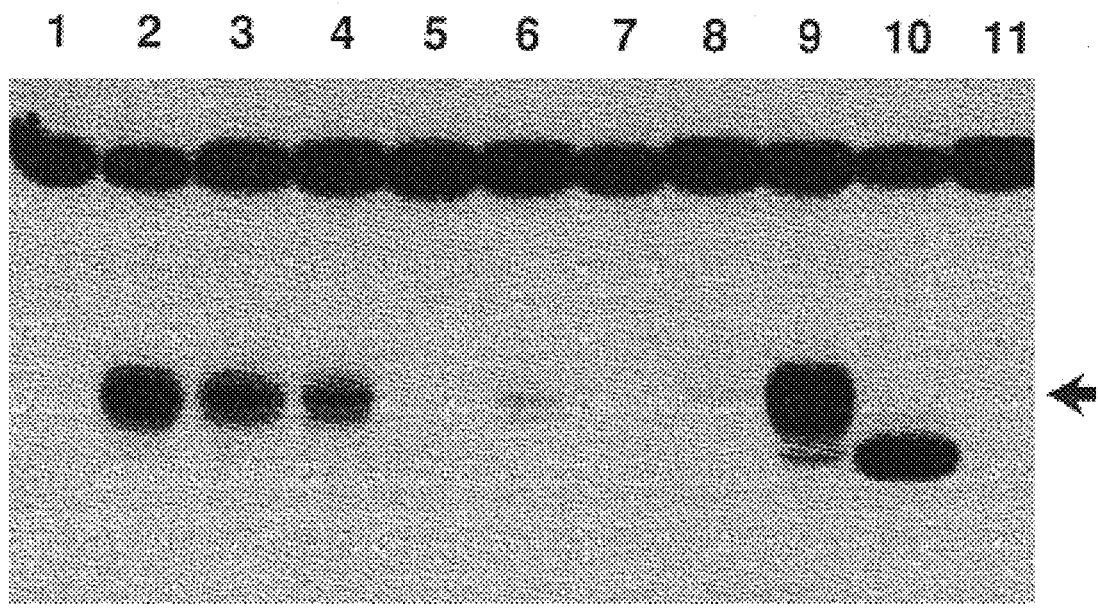
FIG. 3 is a gel showing the sensitivity of MutY enzyme detection of ΔF508 target.

FIG. 3 demonstrates the sensitivity of the invention for the mismatch cleavage detection of a mutant ΔF508 target. The target, the probe, and the assay are described as for the results shown in FIG. 2 above. The assay was carried out with 0 fmole (Lane 1, control), 7 fmole (Lanes 2 and 3), 0.7 fmole (Lanes 4 and 5), 0.07 fmole (Lanes 6 and 7) and 0.007~fmole of ΔF508 target at 37° C. Additional 75 mM of AA was included in Lanes 1, 2, 3, 4, 6, and 8. The rest of assay mixture in lane 2 was incubated at 37° C. for another 20 hr to repeat the experiment of FIG. 2B for quantifying MutY cleavage. An equal volume of stopping dye solution was added to the first half for gel electrophoresis (lane 9). The other half was pretreated with 1 M piperidine at 90° C. for 30 min before adding to the dye solution for gel electrophoresis (lane 10).

FIG. 3 further shows that AA at 75 mM recycles the target and increase the sensitivity. As low as a few amole of target can be identified (lane 8). Because the lowest detection limit with amplifier is 7 amole (lane 8), there is a $10^2$–$10^3$ improvement of sensitivity. Again in the repeated experiment, the assay yields more product than the target in the reaction mixture (lanes 9 and 10).

Example 4

Amplification and Detection for Pathogen Targets

In addition to determining the nature and site of a mutation, the specific G/A cleavage of a probe with known complementary sequence to the target can also identify specific nucleic acid sequences of bacteria and virus targets. However, detection of pathogenic microorganisms in biological samples needs a greater sensitivity due to the very low numbers of DNA copies of the infectious agents in tissues of infected patients. To mimic the conditions of detecting infectious microorganisms by signal amplification, a cloned envelope DNA of several thousand bp from HIV 1 subtype B was used as a target for hybridization to the 21 bp HIV-1b probe to generate a G/A mismatch for cleavage.

Figure 4:
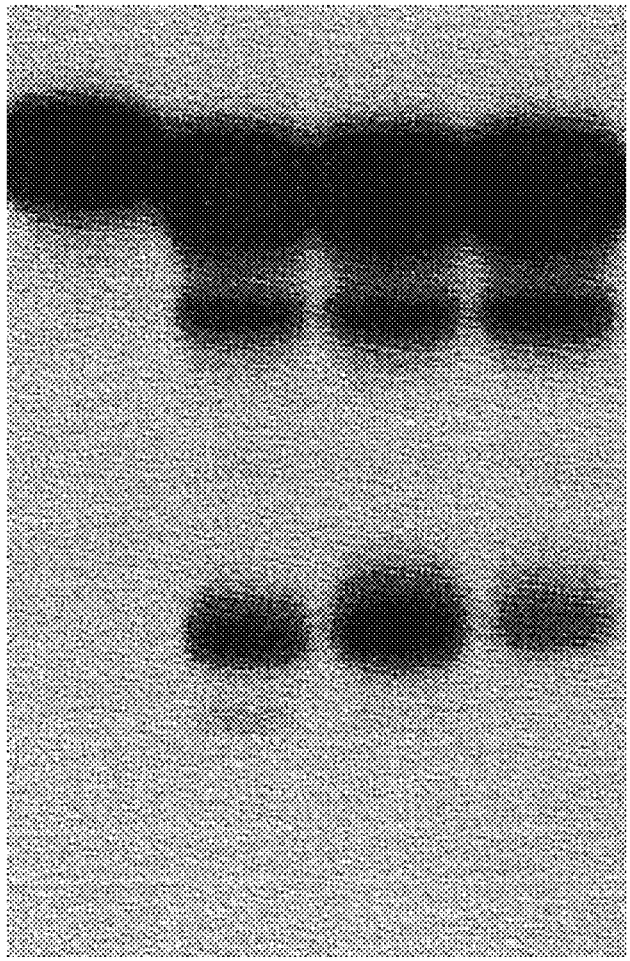
FIG. 4 is a gel showing MutY enzyme detection of HIV 1 subtype B target.

FIG. 4 shows the MutY detection of a HIV 1 type B target. The target is a 7.3 ×$10^3$ bp iff JM109 plasmid harboring a 1643 bp envelope SP160 gene of HIV 1 type B. Approximately, 10 fmole of the target was incubated at 37° C. with AA at 0 mM (Lane 2), 10 mM (Lane 3) and 20 mM (Lane 4). Lane 1 is the control containing no target.

FIG. 4 shows the mutY cleavage of the HIV-1b probe (lane 2) that hybridized the HIV 1 type B DNA target. Once again, MutY enzyme does not cut single-stranded probe (lane 1). It cleaved only the heteroduplex at the A of G/A mismatch. The size of the 11 bp product is correct (lane 2), and thus, confirms the cut at "A" of the mismatch and the identity of HIV envelop sequence. The amplification of sensitivity at 10 mM AA (lane 3) but inhibition of sensitivity at 20 mM (lane 4) in FIG. 4 is an interesting observation. Indeed, inhibition was also observed at 200 mM of AA in the assay of CF target (FIG. 7A, lane 2) and at 20 and 50 mM AA for BT20 target (FIG. 7B lane 4 and 5). Regardless, FIG. 4 further demonstrates the detection of infectious agents with a small probe for a large DNA target.

Figure 7A:
FIGS. 7A and 7B are gels showing the effects of AA concentration on signal amplification of mismatch cleavage.
Figure 7B:
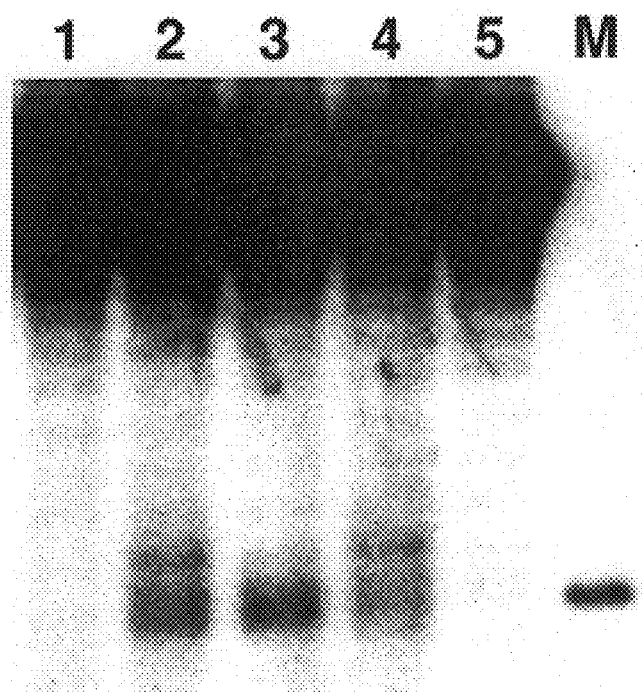

FIG. 7A shows the effects of AA concentration on signal amplification of mismatch cleavage. The concentrations of the probe and the target used in the experiment in FIG. 7A are as described for FIG. 2A. The same assay conditions are carried out with 75 mM of AA (lane 1) and with 200 mM of AA (lane 2). Lane C is the control without the target DNA. There is no observable amplification of mismatch cleavage in the assay with 200 mNM of AA.

FIG. 7B shows the effects of 5 (lane 2), 10 (lane 3), 20 (lane 4) and 50 mM (lane 5) of AA on the amplification of mismatch cleavage for the BT20 probe. Lane 1 is the control. The assay conditions are those as described for the assay used in FIG. 1. The figure clearly shows that AA at 10 mM cause more release of cleaved probe than that at 5 mM and has high amplification. However, the amplification decreases at 20 mM AA. It is even lower at 50 mM AA.

Because AA can increase the Tm, the inhibition may be caused by the increased Tm of the target/product complex at a higher AA concentration. The Tm for hybridization of the probe to a target depends on the buffer salt concentration, the quality and number of base pairs. The following formula provides an estimation of the Tm: Tm=81+16.6 log (Na+)+ 0.41 (%G+C)+0.63(%formamide)−(600/L) (Source: Sambrook, J., et al., *Molecular cloning, A laboratory manual*, 9.50–9.57, 1989). A change of salt concentration from 10 mM to 100 mM will increase the Tm by approximately 16° C. Table 1A lists the Tms for the probes and products. The 21 bp ΔF508 probe has 6 GC pairs whereas the 21 bp probe for HIV target has 11 GC pairs. The Tms of the products from ΔF508 probe are 24–26° C. whereas those from HIV probe are 30–32° C. For recycling of the target and thus amplification of sensitivity to occur, the target must be freed from the enzyme and the cleaved probes. Although high concentrations of amplifier will speed up the dissociation of the target from the enzyme, it also increases the Tm for hybridization of the target with the cleaved probe. Thus, the target will not be freed for recycling at a high AA concentration. Nevertheless, it is observed that a higher assay temperature will eliminate the inhibition indicating a further increase of amplification at a higher temperature with a thermal stable MR enzyme. These data are consistent with the results in FIGS. 7A and 7B and with the mechanism of the amplification shown in FIG. 8 by blocking the enzyme binding sites.

Example 5

Detection and Amplification of MC Products for Probes to RNA Target

Figure 5A:
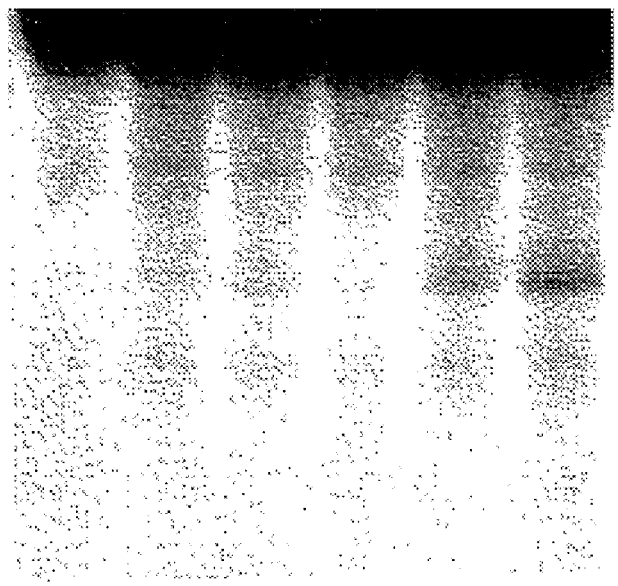
FIGS. 5A and 5B are gels showing cleavage with signal amplification of a G/A mismatch in DNA/RNA heteroduplex.

In addition to identifying the DNA target sequences, the MR enzymes will also cleave the A at the G/A mismatch of a DNA/RNA heteroduplex in detection of a RNA transcript of HCV target. The target RNA is a T7 RNA transcript of 1100 bp in the conserved HCV region. FIG. 5A shows time course and dose response in the MC assay for the HCV RNA transcript.

In the assay, approximately 250 fmole of a 19 base deoxyoligomer probe was incubated at 37° C. with 150 fmole (lanes 3 and 6), 50 fmole (lanes 2 and 5) or 0 fmole (lanes c1 and c4) of HCV RNA target for mutY cleavage. An aliquot of 3 ul assay mixture was withdrawn at 5 hr (lanes 1–3) or 20 hr (lanes 4–6) and added to an equal volume of dye buffer to stop the reaction. The results demonstrate that the amount of the cleaved product is proportional to the concentrations of the RNA target (lanes 1, 2, and 3 or lanes 4, 5, and 6) and the incubation time periods for cleavage (lanes 2 vs 5 or lanes 3 vs 6).

Figure 5B:
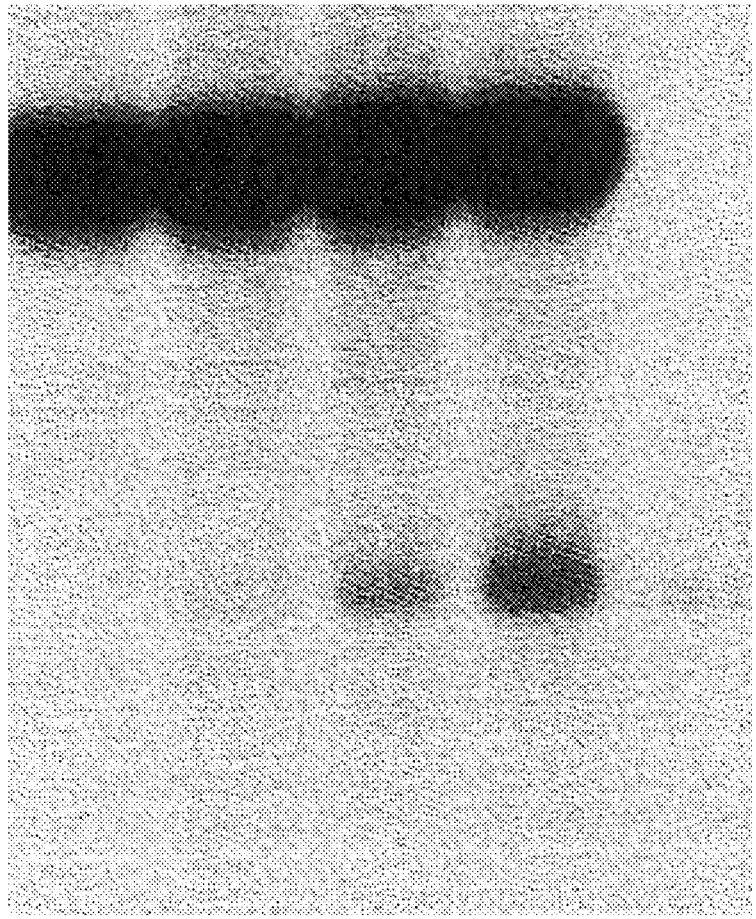

FIG. 5B shows the cleavage with signal amplification of a G/A mismatch in a DNA/RNA heteroduplex. The assay is carried out in reaction mixtures containing a 19 bp probe (200 fmole) and 0 (lane 1, no target control), or 100 fmole of HCV targets (Lanes 24) at 37° C. as described above. The reaction mixtures for lanes 3 and 4 were heated at 90° C. for 3 min. and then cooled to 37° C. before the addition of MutY. Additional AA was included in the assay mixture for lane 4 to a final concentration of 10 mM for signal amplification.

FIG. 5B shows the cleavage (lanes 2–4) of the deoxyoligomer probe in the DNA/RNA heteroduplex and the amplification (lanes 4) of the assay. The detection of the RNA transcript demonstrates that the method can be used to simplify the Northern analysis of RNA. Furthermore, the amplification method of the invention improves the sensitivity to detect a minute quantity of RNA. The cleavage is so specific that the assay can differentiate between two target sequences with a one base difference.

Figure 8:
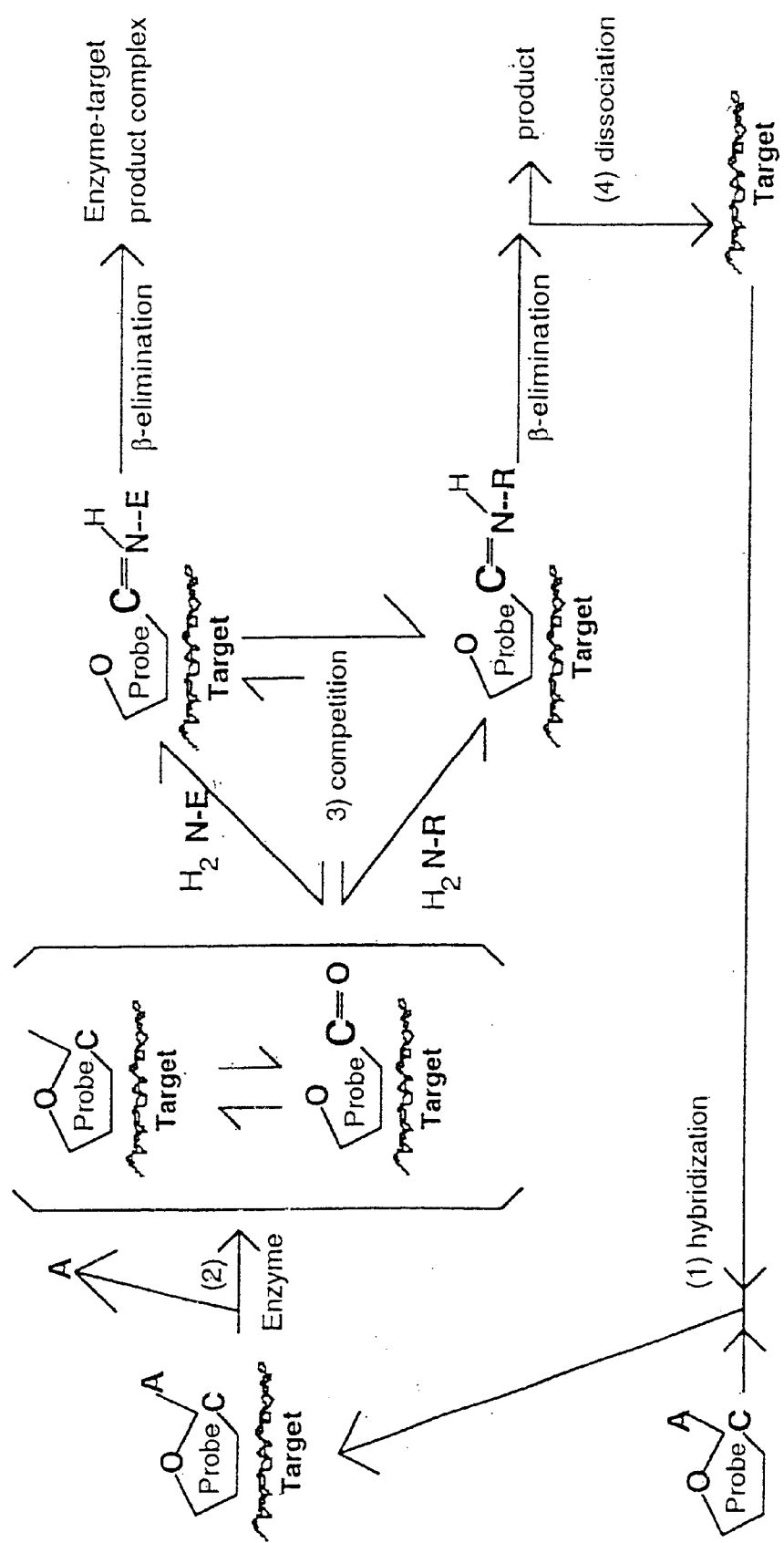
FIG. 8 is a diagram showing a possible mechanism for mismatch cleavage and amplification by AA or amine derivative.

MutY enzyme was first purified to near homogeneity by Modrich et al. (AU, K.G. et al., *Proc. Natl. Acad. Sci.*, 86, 8877–8881, (1989)) and the substrate specificity was determined. They used a circular closed heteroduplex DNA with G/A mismatch as a substrate. This enzyme showed only glycosylase activity that removes "A" base to generate an AP site (apurine-apyrimidine site), but no endonuclease activity to cleave the phosphodiester linkages. The reasons for the discrepancy in enzyme specificity between the observations of Modrich et al., and the present invention are not clear (Hsu, I-C., In: Taylor, G R. (Ed.), *The Detection of DNA Sequence Polymorphisms and Mutations: Methods and Application*, CRC Press, Inc., 1997, pp. 195–206., Lu, A., and Chang, D., *Cell*, 54, 805–812, 1988, and Au, K.G. et al., *Proc. Natl. Acad. Sci.*, 86, 8877–8881, 1989). Regardless, the removal of the A base by the nucleic acid glycosylase will open the deoxyribose ring and present the carbonyl group at $C_1$ of the deoxyribose to an amino group for forming a Schiff base. Piperidine, one of the amines disclosed in our method, has been used in the chemical cleavage method in DNA sequencing by Maxam and Gibert (Maxam, A. M., and Gilbert, W., *Methods in Enzymology*, 65, 499–561, 1980). Thus, the formation of Schiff base can result in the breakage of the phosphodiester linkage on both sides of the AP (apurinic) deoxyribose as observed in our examples. Additionally, binding of MutY with mismatched DNA heteroduplex or its cleaved complex had been demonstrated by non-denaturing low salt acrylamide gel electrophoresis (Lu, A., and Chang, D., *Cell*, 54, 805–812, 1988, and Au, K. G., et al., *Proc. Natl. Acad. Sci.*, 86, 8877–8881, 1989). The hypothesis is that MR enzymes have an amino binding site to form a Schiff base at $C_1$ of the deoxyribose in the AP DNA substrate (Kow, Y. W., and Wallace, S., *Biochemistry*, 26, 8200–8206 1987;Purmel et al., *Mutat. Res.*, 364, 193–207, 1996). This Schiff base formation will then result in the observed binding and cleavage at the site of mismatch (Maxam, A. M., and Gilbert, W., *Methods in Enzymology*, 65, 499–561, 1980). The competition of AA with the MutY for the DNA heteroduplex substrate (FIG. 2A) indicates that the binding site of MutY is an amino group (Jiang et al., *J. Biol. Chem.*, 272, 32230–32239, 1997;Kow, Y. W., and Wallace, S., *Biochemistry*, 26, 8200–8206, 1987). The freeing of the target DNA for amplification is a result of competition between the amines with the amino group binding site in MutY enzyme. Since the Schiff base formation by the addition of amino group to the $C_1$ aldehyde can cause the cleavage of phosphate bonds (Maxam, A. M., and Gilbert, W., *Methods in Enzymology*, 65, 499–561, 1980), our results indicate that, in addition to glycosylase activity, MutY has endonuclease activity and can cut phosphodiester linkages through β elimination of Schiff base formation with the amino group in the enzyme. FIG. 8 depicts the possible mechanism of mismatch cleavage and the amplification by amines.

The shape of DNA in the aqueous solution has profound effects on MR cleavage. The rate and the quantity of cleavage are affected by the environment and the three-dimensional structure of enzyme substrate complex. This phenomenon was previously observed in the use of MR enzyme in screening DNA mutations (Hsu, I-C., In: Taylor, G. R. (Ed.), *The Detection of DNA Sequence Polymorphisms and Mutations: Methods and Application*, CRC Press, Inc., 1997, pp. 195–206, Xu, J. F., et al., *Carcinogenesis*, 17, 321–326, 1996, Hsu, I-C., et al., *Carcinogenesis*, 15, 1657–1662, 1994, Lu, A. and Hsu, I-C., *Genomic*, 14, 249–255, 1992, Kong, D., et al., *Proc. Am. Assoc. for Cancer Res.*, 38, 39, 1997). Therefore, it is likely that Modrich's MutY binds to the carbonyl group in the deoxyribose of the substrate to form a Schiff base. However, the Schiff base formation between the enzyme and their circular closed DNA heteroduplex, the only substrate they used, was stabilized by the assay environments.

The present invention provides for methods of detecting and quantifying specific DNA and RNA targets with great sensitivity through the amplification of the probe product. This amplification is achieved without the use of PCR or RT (reverse transcriptase) steps to amplify the target molecule. Additionally the methods can be practiced under isothermal or temperature cycling assay conditions.

Modifications and applications of the invention will be obvious to those skilled in the art and are intended to be encompassed by the disclosure of the present invention.

While a specific embodiment of the invention has been shown and described in detail to illustrate the application of the principles of the invention, it will be understood that the invention may be embodied otherwise without departing from such principles and that various modifications, alternate constructions, and equivalents will occur to those skilled in the art given the benefit of this disclosure. Thus, the invention is not limited to the specific embodiment described herein, but is defined by the appended claims.

What is claimed:

1. A method for detecting predetermined nucleic acid sequences of a target molecule comprising the steps of:

hybridizing a deoxyoligomer probe molecule to a target molecule to form a complex wherein the complex has at least one site of basepair mismatch or basepair being modified;

reacting the complex with a mismatch repair enzyme to remove an A base, a T base, or other modified bases from the deoxyoligomer probe at the site of basepair mismatch to form an apurinic or apyrimidinic site; and binding an amplifier molecule to the apurinic or apyrimidinic site to cleave a phosphodiester bond from a deoxyribose to form a probe fragment, and freeing said mismatch repair enzyme and target from the substrate complex.

2. A method as in claim 1, further comprising the step of detecting the cleaved probe fragment.

3. The method of claim 1 wherein said target molecule is DNA.

4. The method of claim 3 wherein said DNA is selected from the group consisting of mutant DNA and pathogenic microorganism DNA.

5. The method of claim 1 wherein said target molecule is RNA.

6. The method of claim 5 wherein said RNA is selected from the group consisting of an RNA transcript and a retrovirus.

7. The method of claim 1 wherein said mismatch repair enzyme is selected from the group consisting of a nucleic acid glycosylase and an N-glycosylase.

8. The method of claim 1 wherein said mismatch repair enzyme is selected from the group consisting of MutY, thymidine glycosylase, and glycosylases for removing modified nucleic acid bases.

9. The method of claim 8 wherein said glycosylase for removing modified nucleic acid bases is selected from the group consisting of endo III, endo IV, endo VIII, T4 endonuclease V, and derivatives thereof.

10. The method of claim 1 wherein said amplifier molecule is a low molecular weight amine compound.

11. The method of claim 10 wherein said low molecular weight amine compound is selected from the group consisting of ammonium acetate, diethylamine, piperidine, ammonium carbonate and combinations thereof.

12. The method of claim 1, wherein said method is performed under isothermal conditions.

13. The method of claim 1 wherein said method is performed under conditions of temperature cycling.

14. A method for amplifying a product of mismatch cleavage, comprising the steps of:
 providing a suitable sample of said product of mismatch cleavage, and
 binding an amplifier molecule to apurinic or apyrimidinic probe and blocking the mismatch repair enzyme from accessing the apurinic or apyrimidinic site to free said enzyme and target from the enzyme-target/product complex for recycling.

15. A method as in claim 14 wherein said amplifier molecule is selected from the group consisting of an ammonium acetate, an amine derivative and combinations thereof.

16. A method as in claim 14 wherein said amplifier molecule is selected from the group consisting of ammonium acetate, diethylamine, piperidine, ammonium carbonate and combinations thereof.

17. A method as in claim 14 wherein said amplifier molecule is ammonium acetate.

18. A kit for amplifying mismatch repair enzyme cleavage products comprising:
 a deoxyoligomer probe molecule,
 a buffer solution,
 a mismatch repair enzyme, and
 an amplifier molecule.

19. A kit as in claim 18 wherein said mismatch repair enzyme is selected from the group consisting of MutY, thymine N-glycosylase, and glycosylase for removing modified nucleic acid bases.

20. The kit of claim 19 wherein said glycosylase for removing modified nucleic acid bases is selected from the group consisting of endo III, endo IV, endo VIII, T4 endonuclease V, and derivatives thereof.

21. A kit as in claim 18 wherein said amplifier molecule is selected from the group consisting of ammonium acetate, diethylamine, piperidine, ammonium carbonate and combinations thereof.

22. A method for detecting a predetermined nucleic acid sequences of a target molecule comprising the steps of:
 hybridizing a deoxyoligomer probe molecule to a target molecule to form a hybrid duplex wherein the duplex has at least one site of basepair mismatch, or modification,
 reacting the duplex with a mismatch repair enzyme to form a enzyme substrate complex,
 binding an amplifier molecule to the complex so as to cleave the probe and release the probe fragment for detection and for inducing secondary amplification.

23. A method for detecting predetermined nucleic acid sequences of a target molecule comprising the steps of:
 hybridizing a deoxyoligomer probe molecule to a target molecule to form a complex wherein the complex has at least one site of basepair mismatch or basepair being modified;
 reacting the complex with a mismatch repair enzyme to remove an A base, a T base, or other modified bases from the deoxyoligomer probe at the site of basepair mismatch to form an apurinic or apyrimidinic site;
 and binding a target freeing agent to the apurinic or apyrimidinic acid site to cleave a phosphodiester bond from a deoyribose to form a probe fragment, and freeing said mismatch repair enzyme, the cleaved probe fragment and target from the substrate complex;
 wherein said method is performed under isothermal conditions.

24. A method as in claim 22 wherein said isothermal conditions are at a temperature that is lower than the Tm of the probe-target complex.

25. A method as in claim 1, further comprising the addition of an amine amplifier to cleave the phosphodiester of the probe at a mismatch site.

* * * * *